United States Patent [19]

McDonald

[11] Patent Number: 5,534,431
[45] Date of Patent: Jul. 9, 1996

[54] HYBRIDOMAS AND MONOCLONAL ANTIBODIES SPECIFIC FOR UNIQUE DETERMINANTS OF NEPHROPATHY-RELATED IMMUNOGLOBULIN G AND COMPLEXES THEREOF

[75] Inventor: Thomas L. McDonald, Omaha, Nebr.

[73] Assignee: The Board of Regents of the University of Nebraska, Lincoln, Nebr.

[21] Appl. No.: 202,904

[22] Filed: Feb. 28, 1994

[51] Int. Cl.$^6$ .............................. C12N 5/20; C07K 16/42; G01N 33/53
[52] U.S. Cl. .................. 435/240.27; 435/7.1; 435/172.2; 435/70.21; 530/388.25; 530/391.1
[58] Field of Search .............................. 424/130.1, 140.1; 435/240.27, 172.2, 70.21, 7.1; 530/388.25, 391.1

[56] References Cited

PUBLICATIONS

Kofoed–Enevoldsen et al., Transcapillary filtration of plasma protein in long term type I (insulin dependent) diabetic patients. Scnad. J. Clin. Lab. Invest. vol. 52, pp. 591–597, 1992.

*Primary Examiner*—Paula K. Hutzell
*Attorney, Agent, or Firm*—Zarley, McKee, Thomte, Voorhees, & Sease

[57] ABSTRACT

A novel immunoglobulin-like glycoprotein is described which has been found to occur in high concentrations in the urine of patients with glomerulosclerosis of end-stage renal disease. This nephropathy-related protein is also found at a high frequency in the urine of patients with a high risk of developing kidney disease, as well as in the urine of kidney transplant recipients who are experiencing early signs of organ failure or rejection. Although this glyco-protein has several antigenic epitopes which are identical to those on normal human IgG molecules, two monoclonal anti-bodies have been developed which bind epitopes which are unique to this nephropathy-related immunoglobulin-like molecule. Immunometric assays have been developed which permit this nephropathy-related protein to serve as an early and specific marker for kidney-related diseases.

6 Claims, 1 Drawing Sheet

HYBRIDOMAS AND MONOCLONAL ANTIBODIES SPECIFIC FOR UNIQUE DETERMINANTS OF NEPHROPATHY-RELATED IMMUNOGLOBULIN G AND COMPLEXES THEREOF

BACKGROUND OF THE INVENTION

The present invention relates to novel immunological reagents and their use in assays for the detection of kidney disease or damage (hereinafter also sometimes called "nephropathy"), and, in particular, assays capable of detecting nephropathy at developmental stages not possible to detect with current methodologies. Fundamental to the present invention is the discovery of a human nephropathy-related protein which is a glycoprotein in the immunoglobulin class of globular proteins and which has been demonstrated to be associated with development of overt kidney disease. This nephropathy-related immunoglobulin-like protein (hereinafter referred to as "NRIg") is believed to be capable of serving as a very early and specific marker for kidney-related diseases.

Thus, in one embodiment, the present invention relates to the isolation and purification of NRIg from human body fluids using the immune complex-capturing protein reagent described as "RhC" in U.S. Pat. No. 4,783,528.

In another embodiment, the invention relates to the use of NRIg in its purified form for the preparation of highly specific antibodies for use in the assays of the present invention. An especially preferred embodiment of the present invention relates to the use of such antibodies, and immobilized RhC, in a unique and highly sensitive immunologic assay for detecting and/or determining the concentration of NRIg in urine as a predictor of the development of overt nephropathy.

In yet another embodiment, the present invention provides simple, economical, and reliable assays for the detection of NRIg in biological fluids. These assays utilize the monoclonal antibodies of this invention. Because of their specificity for NRIg, these antibodies are particularly useful for the detection of kidney disease in a wide variety of clinical settings by a variety of methods ranging, for example, from sophisticated enzyme-linked immunosorbant assays (EIA) to elegant and simple radial immunodiffusion (RID) assays.

The immunologic terms employed herein are believed to be in accord with conventional usage and definition. Should any presently unforeseen confusion arise, unless otherwise indicated, the construction of a term shall be in accordance with its definition and usage in the well known textbook by William E. Paul, *Fundamental Immunology*, second edition (1989), Raven Press Ltd, New York.

For the convenience of the reader, several publications are referenced in the present discussion. While these references will more fully describe the state of the art to which the present invention pertains, the inclusion of these references is not an admission that any represent prior art with respect to the present invention.

The clinical diagnosis of kidney disease as currently practiced relies almost exclusively on observed changes in levels of blood urea nitrogen (BUN) and of creatinine in plasma, as well as on abnormalities detected in urinalysis, and on measured changes in urine output. While these tests are useful in revealing existing renal damage, they are not useful in predicting future kidney damage.

The present discussion will serve to illustrate the difficulties which clinicians and research investigators alike face in accurately detecting kidney disease very early in its development, i.e., in its incipient form, not only in individual patients without a history of intrinsic renal disease, but especially in those patients whose systemic illness will likely, at some point during the course of their disease, affect the kidneys.

The underlying pathogenic mechanism(s) of most kidney disease is not known, in spite of the wide occurrence of this clinical phenomenon, and despite extensive clinical and laboratory investigation into the problem. Given the wide occurrence of pathological conditions which may affect the kidneys, it is surprising that there still is no single noninvasive diagnostic test of a measureable substance which can be used to predict with confidence which individuals will develop nephropathy as a complication of their primary disease. Such a diagnostic test for incipient nephropathy should constitute an "early warning signal," when medical intervention could still limit the extent of subsequent kidney damage.

Toward this end, much effort has been devoted to the measurement of low-molecular weight plasma proteins, such as beta-2-microglobulin in the urine or serum, or to the determination of a variety of renal enzymes, such as L-alanine aminopeptidase (AAP) and N-acetyl-beta-D-glucosaminidase (NAG) which are released into the urine when renal injury occurs. Although these tests have provided much useful information, they have had limited application, not only because they are nonspecific with regard to the cause and site of renal injury, but also because the test proteins are not very stable in urine. Furthermore, a variety of enzyme inhibitors and other interfering materials are usually present in urine, and this significantly reduces the specificity and usefulness of these tests.

To improve the usefulness of noninvasive tests, several investigators have developed immunologic measurements of specific renal antigens present in the urine in order to determine not only the occurrence of nephropathy, but also the site and severity of the renal injury. For example, Schoenfeld and Glassock (Kidney Intl 3: 309–314, 1973) developed an immunodiffusion technique to identify a proximal tubule brush-border epithelial antigen in concentrated human urine. Zager and colleagues extended this work by developing a radioimmunoassay for a proximal renal tubular epithelial antigen (termed HRTE-1) in urine. The assay (Nephron 26: 7–12, 1980) lacked specificity, however, because this antigen could be detected in organs other than kidney.

A number of investigators have reported on the use of monoclonal antibodies as probes for detecting the presence of specific kidney-related antigens in serum and urine (Sachse et al., Clin Chim Acta 110: 91–104, 1981; Michael et al., Kidney Intl 24: 74–86, 1983; Tolkoff-Rubin, Kidney Intl.29: 142–152, 1986). The use of these antibodies provided a quantitative means of determining both the site and degree of nephropathy. Because serial samples of urine are readily obtained, this approach permitted monitoring the stage and activity of kidney diseases, as well as its responsiveness to therapy. For example, the use of monoclonal antibodies to detect the 120 kDa proximal tubule antigen, adenosine deaminase binding protein (ABP), which is released from renal brush border epithelial cells into the urine in renal disease, has been described in U.S. Pat. No.

4,731,326. The shortcoming of a number of these assays for detecting the presence of renal proteins in urine, however, is that the antigens being detected are not useful as very early predictors of incipient kidney disease; rather, the assays are useful primarily in determining the type and location of clinically overt nephropathy.

In the group of patients with diabetes mellitus, approximately 35 percent of patients will develop kidney disease and progress to end-stage renal disease approximately 15 years after the onset of diabetes. Unfortunately, the kidney disease in these individuals is usually very advanced and irreversible by the time it is diagnosed by the markers currently being used, which are the persistent presence of an excess of serum proteins (such as albumin) in the urine, and an elevated level of creatinine in the blood.

"Albustix"-positive proteinuria in the urine of diabetic patients, a condition often referred to as macroproteinuria or macroalbuminuria, normally signals the presence of overt clinical nephropathy. Many of the patients who exhibit this advanced-stage of kidney dysfunction also have elevated blood pressure. Kidney biopsies taken at this stage in the disease process usually show advanced and irreversible structural damage to the kidney, and it is very likely that this damage was present in the kidney long before it was detected clinically by the occurrence of proteinuria.

In contrast to this late detection of macroproteinuria, some investigators are advancing the notion that the detection in urine of very small amounts of albumin (microalbuminuria) is a more sensitive marker for kidney disease (e.g., see Mogensen CE. *Diabetes* 39: 761–767, 1990). Unfortunately, exercise, poor control of blood sugar levels, and other metabolic imbalances can nonspecifically increase the albumin excretion in diabetic subjects, thereby reducing the clinical value of microalbuminuria as a reliable single marker of early kidney disease in these individuals. Furthermore, strenuous exercise in itself is sufficient to induce microalbuminuria in the urine of some healthy individuals.

It would be of great clinical benefit to have a test for detecting a substance that is associated specifically with the beginning stages in the development of nephropathy, even before the renal damage becomes a clinical problem. Such early detection of nephropathy is critically important so that appropriate therapy can be initiated in these patients before significant kidney damage has occurred. When kidney disease has been detected early in experimental groups, successful therapy has resulted in the stabilization of progressive kidney disease. Clearly, the very great benefits to be derived from early detection of nephropathy within defined clinical populations mandates the development of detection systems more specific than microalbuminuria.

The potential for the use of the NRIg as an early marker for kidney disease is highly significant. The test for a protein marker other than albumin in the urine of patients as an indicator of the early development of kidney disease would enable the physician to differentiate between the initiation of kidney disease and exercise-induced or incidental albuminuria that can occur sporadically in patients with any of a variety of diseases. Also, a specific marker for end-stage renal disease would be highly beneficial for monitoring and evaluating treatment modalities in clinical trials, and would also identify high-risk patients who would benefit from such therapies.

SUMMARY OF THE INVENTION

In the present invention, the term "body fluids" includes any such fluid which contains detectable amounts of immunoglobulin G (IgG). In general, such fluids include urine, serum, and plasma (the latter simply being serum that has not had consummable clotting factors removed). Urine is the body fluid especially preferred for use in the present invention. While tears, saliva and other mucous secretions are body fluids, and usually contain only IgA immunoglobulin molecules, they may contain immune complexes, or immunoglobulin molecules of either the IgG or IgM isotypes. Cerebrospinal fluid, as another body fluid, rarely contains immunoglobulins, and its use for routine study is extremely impractical due to the significant risks of infection and/or bleeding associated with the invasive procedures utilized to obtain said fluid.

Much of the following discussion will focus on studies in patients with clinically-confirmed diabetes mellitus, since this was the clinical pathological entity in which the novel nephropathy-related protein of the present invention was discovered. However, the novel nephropathy-related protein of the present invention is also associated as an early detector of incipient kidney disease in a variety of clinical pathologies other than diabetes (e.g., amyloidosis; hypertension; and rheumatological disorders, including Systemic Lupus Erythematosus), besides also being an early indicator of organ rejection in patients who received a kidney transplant.

In accordance with the present invention, a protein marker has been found in the body fluids of patients with incipient nephropathy, including a number of patients without clinical symptoms of kidney disease. The presence of this marker correlates exactly with the onset and progression of nephropathy. Using the "RhC" immune complex-capturing reagent, the nephropathy-related marker protein of this invention was first isolated as part of a circulating immune complex (CIC) from serum of diabetic patients with end-stage renal disease. The resulting complex constitutes an embodiment of the present invention. In such a complex, the nephropathy-related NRIg protein is an essential component of the CIC. NRIg and its preparation are discussed more fully hereinafter.

In brief, NRIg has a molecular weight of about 150,000 daltons (hereinafter "150 kDa"), and is an immunoglobulin G (IgG). This is very unexpected because an immunologic basis for diabetic nephropathy has never been established. Even more unexpected is the early pre-symptomatic appearance of this NRIg protein marker in body fluids of patients who subsequently develop nephropathy. This unexpected phenomenon forms the basis for the immuno- logic assays for the early detection of nephropathy of the present invention. Such immunologic assays are dependent upon antibodies with appropriate specificities, preferably, the monoclonal antibodies provided in accordance with the present invention and discussed more fully hereinafter. All of these antibodies are highly specific for distinct antigenic determinants on the NRIg molecule.

NRIg is an immunogenic protein, and expresses unique antigenic determinants which are useful in inducing the production of polyclonal and monoclonal antibodies. For such antibody production it is preferred that NRIg be used in a purified form, and, in such form, constitutes an embodiment of the present invention. In a purified form, the NRIg glycoprotein is removed from its native state by procedures which will specifically concentrate this protein to >1 ug/ml. For the production of specific antibodies, it is preferred that the concentrations of NRIg be >10 ug/ml. The antibodies produced as a result of immunizing suitable host animals with purified NRIg are capable of binding specifically and with very high affinity to the antigenic determinants expressed on NRIg. The binding affinities of the antibodies of the present invention are generally at east $10^6$ liters/mole, preferably at least $10^8$ liters/mole and more preferably $10^9$ liters/mole.

In summary, NRIg is derived from a body fluid of an host organism suffering from a nephropathy-related disorder. Upon the occurrence of such clinical disorders, native immunogenic NRIg protein is found in several body fluids, including serum and urine of the host organism. Of particular importance is the unexpected finding that native NRIg can be found in serum and urine of individuals even before clinical symptoms of kidney disease appear, making NRIg useful not only as a detector of incipient kidney disease, but also as a sensitive and early predictor of the development of kidney disease.

In producing monoclonal antibodies in accordance with the present invention, hybridoma cell lines have been established which synthesize and secrete monoclonal antibodies specific to the NRIg protein of this invention. As a first step in the production of such monoclonal antibodies, animal hosts are immunized according to a conventional protocol in order to induce the development of specifically immune lymphocytes (known as plasma cells) which produce antibodies to the NRIg. These lymphocytes are recovered from the immunized host and are fused according to conventional experimental protocols with myeloma tumor cells derived from the same animal species to form giant somatic cell hybrids. These hybrid fusion protocols, originally reported by G Kohler and C Milstein (Nature 256: 495–497, 1975) are generally known by those skilled in the art.

The cell-cell hybrids exhibit characteristics of both parent cell types used in the fusion: like the malignant myeloma parent, fused cell hybrids have the capacity to grow rapidly and indefinitely in tissue culture; in addition, they have the capacity to secrete large amounts of the antibody specified by the genes of the normal antibody-secreting lymphocyte parent that participated in the fusion. These hybrid cell lines are called "hybridomas." After appropriate selection and cloning, they are propagated in tissue culture or in a genetically identical or immunocompromised animal for an indefinite period in order to continuously produce antibody to NRIg. One of the established hybridoma cell lines of the present invention secretes an immunoglobulin of the IgM isotype, and has been deposited on Jul. 3, 1990 with the American Type Culture Collection (ATCC) 12301 Parklawn Drive Rockville, Md. 20852, as hybridoma cell line deposit No. HB-10490. Another established hybridoma cell line of the present invention secretes an immunoglobulin of the IgG1 isotype, and has been deposited on Jul. 3, 1990 with the ATCC as hybridoma cell line deposit No. HB-10491. These cell lines constitute an embodiment of this invention.

In another embodiment of the present invention, there is also provided a set of antibodies comprising at least two antibodies of differing isotypes which are useful in sandwich-type immunometric assays which require at least 2 antibodies. Such antibodies exhibiting specific and high affinity binding to antigenic determinants uniquely expressed on the human NRIg of the present invention. It is preferred that this set be made up of homogeneous preparations of antibodies with high affinity for NRIg. An especially preferred embodiment of the present invention comprises a set of such antibodies, wherein at least one is a murine-derived monoclonal antibody of the macroglobulin type, being an immunoglobulin M (IgM) isotype equivalent to the monoclonal antibody produced by ATCC hybridoma cell line deposit No. HB-10490, and at least one other antibody of this set is a murine-derived monoclonal antibody of the immunoglobulin G type 1 (IgG1) isotype equivalent to the monoclonal antibody produced by ATCC hybridoma cell line deposit No. HB-10491. In general, only 2 NRIg-specific antibodies meed be employed. Because each antibody of this set is specific for different antigenic sites and will therefore bind to a different antigenic determiniant on the target NRIg molecule, the set of monoclonal antibodies is uniquely adapted for use in conventional "two-site" or "sandwich" immunometric assay techniques (e.g., see U.S. Pats. No. 4,376,110 and 4,486,530) for determination of the presence and/or concentration of NRIg in body fluids.

In order that they be easily detectable in certain assays, the antibodies of the present invention can be labeled with any of a variety of standard substances which include radioactive, fluorescence, or enzyme markers. Examples of such standard markers are:

1. Radioactive: tritium, carbon-14, phosphorus 32, iodine-125;
2. Fluorescent: fluorescein, rhodamine, phycoerythrin, Texas red;
3. Enzyme: Horseradish peroxidase, alkaline phosphatase, B-galactosidase Methods for labeling antibodies with these markers, and for detecting such markers, are discussed more fully hereinafter, but are generally well known in the art.

In order to carry out certain of the immunometric assays of the present invention, it is necessary to employ an NRIg-specific capturing reagent (i.e., the antibodies of this invention, or RhC ) in an insolubilized form. When thus employed, such NRIg-capturing reagents are insolubilized, or otherwise supported, on a variety of standard immobilization substrates. Examples of materials to which the capturing agents can be attached are glass, synthetic polymers, synthetic resins, cellulose and various metals. Procedures for attaching these capturing agents will vary depending upon the agent and substrate employed, but, in general, are well known in the art. Some of the methods for binding of antibodies to a solid matrix are discussed in E Harlow and D Lane, *Antibodies: A Laboratory Manual*, New York: Cold Spring Harbor Laboratory, pp. 511–552, 1988. However, it is to be noted that with respect to RhC, it was unexpectedly found that binding of RhC to plastic microtest plates (e.g., "Immulon-2" plates made by Dynatech, Chantilly, Va.) requires critical conditions, as discussed more fully hereinafter. In brief, these are the use of a specially-prepared TRIS buffer (containing Tris-2-amino- 2-hydroxymethyl-1,3-propanediol) during the immobilization of RhC to the plastic surface, as well as a requirement that the process be done at an ambient room temperature near 25° C. during the immobilization step. The inert material to which the antibody or RhC is attached or otherwise insolubilized can have an extensive, continuous form, such as a membrane or sheet which is either flat or molded into convenient shapes such as dishes or multiwell plates, or it can be in the form of discrete particles or beads of desired size.

NRIg can be detected in a number of immunometric assays. In an especially preferred embodiment of the present invention, there is provided a simple, economical, sensitive and reliable assay for early detection of kidney disease in which RhC is used as the capturing agent specific for the NRIg protein. The immobilized RhC protein captures and binds any NRIg in the test sample. A labeled antibody, which exhibits immunologic specificity for the NRIg, is then added to the sample to confirm and mark the presence of any NRIg bound to the RhC protein. Thus, in accordance with this embodiment there is provided a process for the determination of the presence of NRIg in a test sample of body fluid comprising the steps:

(A) contacting RhC protein with an inert substrate which is insoluble in the body fluid being analyzed, under conditions which permit the RhC protein to bind to the substrate in order to form an immobilized RhC reagent. This reagent is unlabeled;

(B) contacting a sample of body fluid with the immobilized reagent in order to form insolubilized complexes containing the immobilized RhC protein reagent and any NRIg which may have been present in the test sample;

(C) contacting these insolubilized complexes with a first antibody which binds to said NRIg. This first antibody may be labeled or unlabeled;
  (1) when the first antibody is labeled, measuring either the amount of labeled antibody bound to the insolubilized complexes or the amount of unreacted labeled antibody;
  (2) when the first antibody is unlabeled, contacting the first antibody with a labeled second antibody which binds solely and specifically to the first antibody, and measuring either the amount of labeled second antibody bound to the first antibody, or the amount of unreacted labeled second antibody, and (D) relating the amount of labeled antibody bound to the insolubilized complexes from the test sample with the amount of labeled antibody bound to insolubilized complexes from a positive or negative control sample prepared in accordance with steps (A)–(C), to determine the presence or concentration of NRIg in the test sample of body fluid.

Thus, in summary, this invention provides an immunometric assay process to determine, in a sample of body fluid, the presence or concentration of an antigenic substance associated with the subsequent development of nephropathy, comprising forming a complex of the antigenic substance, RhC protein and an antibody bound to the antigen at a different site than the RhC protein. This complex is formed by contacting the sample of body fluid with the immobilized RhC protein, followed by subsequent contact with an antibody which has binding specificity for NRIg.

Another assay of this invention involves using NRIg specific antibody as the capturing agent. An example of such an assay is an enzyme-linked immunosorbant assay (EIA) which uses either polyclonal or monoclonal antibodies specific for NRIg and immobilized onto an inert substrate to capture the NRIg. A second polyclonal or monoclonal antibody specific for NRIg is then added to the sample to confirm and mark the presence of NRIg bound to the first antibody. This second antibody is labeled with an enzyme suitable for detection by a conventional EIA plate reader (e.g., Dynatech automated EIA plate reader, Dynatech Laboratories, Chantilly, Va.).

The antibodies used in an EIA assay as the unlabeled antibody bound to a solid support and the antibody used as the soluble labeled antibody are usually two or more different monoclonal antibodies, i.e., each antibody specific to a single antigenic site and separately produced by clones derived from unique cell lines. In a preferred embodiment, the monoclonal antibody used as the antibody bound to a solid support is the product of a different cell line than is the monoclonal antibody used for the labeled antibody and the two monoclonal antibodies are selected to bind the NRIg at sites remote from each other so as to not interfere with the other's binding to the antigen.

It has been found convenient to utilize the set of monoclonal antibodies discussed above in an EIA assay adapted for the detection of NRIg. Briefly, this assay is carried out as follows:

a. Purified IgM monoclonal antibody specific for NRIg is coated onto wells of an EIA plate by incubation of the said antibody in the wells for from 1 hr to 24 hr, followed by thorough washing of the wells to remove all unbound IgM antibody.

b. The body fluid to be tested for NRIg content is diluted 1:5 in phosphate-buffered saline containing Tween-20 (PBS-Tween). The diluted test specimen is then incubated in the appropriate wells of the EIA plate for 1 to 2 hr at 37° C. Any and all unbound proteins are removed from the test wells by thorough washing with PBS-Tween.

c. In defining the background for the assay system, a substantial number of body fluid specimens from healthy individuals must be included among the test samples and used as negative controls. This provides information about the range of normal responses which occur in the assay system under the experimental conditions being used.

d. The second unique monoclonal antibody of the present invention which is specific for NRIg is an IgG antibody. It is added to all appropriate wells of the EIA plates and incubated for at least 1 hr at 37° C.

e. Excess (unbound) IgG antibody is washed away with PBS-Tween and a peroxidase enzyme-conjugated goat anti-mouse IgG is added to all test wells, and incubated for 1 hr at 37° C.

f. The EIA plates are again thoroughly washed, and enzyme activity bound to the wells is detected by incubating the plates with the appropriate enzyme substrate such as tetramethylbenzidine (TMB) (see N Rose, H Friedman, and J Fahey: *Manual of Clinical Laboratory Immunology*, 3rd edition, Washington D.C.: American Society for Microbiology Press, pp105–107, 1986) for 0.5–1 hr at 37° C. The amount of reaction product generated in the wells by the reaction of the antibody-bound enzyme and its substrate is quantitated by scanning the entire plate in an EIA reader at an absorbance wavelength appropriate for the particular enzyme-substrate reaction product, such as 450 nm for TMB.

g. The presence of and intensity of an enzymatic color change in an individual well is directly proportional to the amount of human NRIg originally present in the sample of body fluid in that well.

Thus, in summary, the EIA assay is a process for the determination of the presence of NRIg in a test sample of body fluid comprising the steps:

(A) contacting a first antibody with specificity for NRIg with an inert substrate which is insoluble in the body fluid, under conditions which permit the first antibody to bind to the substrate in order to form an immobilized first antibody. This first antibody is unlabeled;

(B) contacting a sample of the body fluid with the immobilized first antibody to form an insolubilized complex of the first antibody and any NRIg present in the sample;

(C) contacting the insolubilized immune complex with a second antibody which binds to the NRIg at an antigenic site different than that bound by the first antibody. This second antibody may be labeled or unlabeled;
  (1) when the second antibody is labeled, measuring either the amount of labeled antibody bound to the insolubilized complex or the amount of unreacted labeled antibody;
  (2) when the second antibody is unlabeled, (a) contact the second antibody with a labeled third antibody which binds solely and specifically to that second antibody, and measuring either the amount of labeled antibody bound to the second antibody, or the amount of unreacted labeled antibody; and (D) relating the amount of labeled antibody bound to insolubilized complexes from the test sample with the amount of labeled antibody bound to insolubilized complexes from a positive or negative control sample prepared in accordance with steps (A)–(C), to determine the presence or concentration of NRIg in the test sample of body fluid.

In addition, the target human NRIg protein can be detected by a radial immunodiffusion (RID) assay. This assay can be set up for the simultaneous detection and quantitation both of microalbuminuria and of NRIg in the same sample of a body fluid. As a first step in the preparation of this assay, a suitably-diluted antibody or combination of antibodies to NRIg is suspended in agarose gel in part of the assay vessel, and a suitably-diluted antibody or combination of antibodies to albumin is separately suspended in agarose gel in another part of the assay system. An aliquot of the body fluid to be tested is applied into small wells individually cut into each of the different agarose types. As the diluted body fluid sample diffuses into the agarose, a ring of precipitation will form at a distance from the center of the well which is proportional to the concentration of the antigen in the body fluid. By means of a previously determined standard curve, the diameter of the immunodiffusion ring can be quantitatively related to the concentration either of NRIg or of albumin in the body fluid being tested. Polyclonal antibodies are preferred because of their enhanced capacity to precipitate antigen in agar (as discussed in W Paul, *Fundamental Immunology, 2nd edition*, New York: Raven Press, page 338, 1989).

Also, included in the scope of the present invention, one can employ inhibition assays for the detection of the presence or concentration of NRIg in a test sample of body fluid. In such assays, a known quantity of NRIg and monoclonal antibody is contacted with a sample suspected of containing NRIg. The extent to which formation of immune complexes between the known antibody and the known NRIg is inhibited is directly proportional to the amount of competing NRIG antigen present in the test sample assayed. In a preferred embodiment of an inhibition assay, the antiNRIg antibody is in solution and the NRIg antigen is bound to insoluble particles such as, for example, red blood cells, or latex particles of a size which permit visible aggregates to form. In the absence of any competing NRIg antigen, the anti-NRIg antibodies present in the solution will cause the NRIg-coated particles to aggregate and form visible clumps (which, for the sake of the present discussion, will be called agglomerates hereinafter). When a test sample of body fluid suspected of containing NRIg antigen is mixed with the anti-NRIg antibody and the bound NRIg antigen, inhibition of agglomerate formation occurs because of complexing between the antibody and the soluble NRIg antigen which cannot form agglomerates. The reduction in agglomeration can be measured using turbidimetric techniques, such as nephelometry.

It is to be understood that in any of the assays of the present invention, all of the assays can be used to detect the presence or the concentration of NRIg, i.e., they can be used to detect or to measure NRIg qualitatively or quantitatively, respectively. Thus, the terms "measure" and "measuring", and "detect" and "detecting" as used above and hereinafter are meant to cover both the quantitative and the qualitative aspects of the assays.

DETAILED DESCRIPTION OF THE INVENTION

Nephropathy-related immunoglobulin protein (NRIg)

Figure 1:
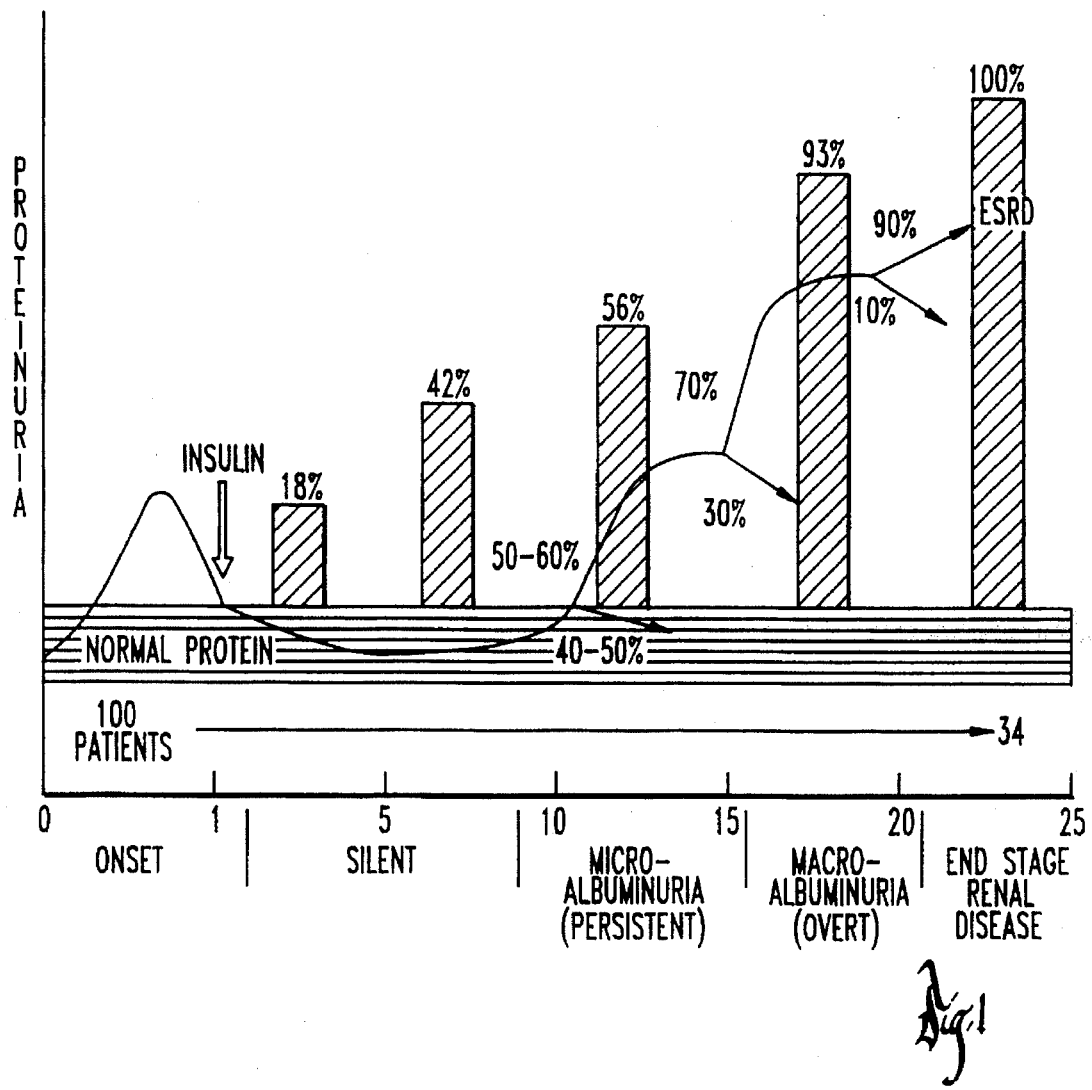
FIG. 1 summarizes data relating to the frequencies of NRIG and microalbuminuria in Type I diabetics at different durations of diabetes and at different levels of proteinuria. The solid line represents the frequency of albuminuria at different durations of diabetes as predicted from epidemiological studies. The frequencies of NRIg in the Type I diabetics in this study at different durations of diabetes and at different levels of proteinuria are shown by the hatched bars. The numbers at the top of the bars show the percentage of NRIg-positive patients at a given duration as kidney disease progresses.

NRIg is found at elevated levels in the body fluids of a host organism which is suffering from a nephropathy-related disorder which produces the protein. It is not been found at elevated levels in normal, healthy individuals.

Although the following discussion will focus on studies in patients with diabetes mellitus (since this was the disease entity in which the nephropathy-related protein of this invention was discovered), it is not intended to limit the present invention to diabetes only. Included within the scope of this invention is any disease in which this protein is produced.

Among the diseases in which this novel NRIg protein appears are those which involve vascular sclerosis. These diseases are diabetes, hypertension, and some of the rheumatic diseases, such as amyloidosis, among others. By "vascular sclerosis" is meant any physiologic scarring and blockage of microvasculature which occurs when the body deposits collagen and fibroblasts during biological repair processes which occur at the site of a biological lesion.

NRIG characteristics.

Prevalence. The NRIg protein of the present invention has been found to occur in high concentrations in the urine of all diabetic patients with glomerulo-sclerosis of end-stage renal disease. It also has been found at a high frequency in patients with a high risk of developing kidney disease, such as: diabetic patients with microalbuminuria and a duration of disease of approximately 15 years or longer, patients with chronic hypertension, and rheumatoid arthritis patients undergoing gold therapy.

Unexpectedly, NRIg has also been found in the urine of approximately 20% of diabetics who are without clinical laboratory evidence of kidney disease or microalbuminuria (range, 21% of Type I and 19% of Type II diabetics); the appearance of NRIg in these patients may well be an indication that clinically-undetectable incipient nephropathy is present. This is supported by data which show that as the level of albumin in the urine of patients increases from normal low levels to macro levels, the percentage of patients with NRIg in their urine also dramatically increases, exactly in parallel with the increase in risk of end-stage renal disease. NRIg appears then, to be a valuable predictor of impending development of overt kidney disease. The distribution frequency of NRIg in Type I and Type II diabetic patients, and in patients with hypertension, at different levels of albuminuria is summarized in Table 1, where the increase in albuminuria from normal levels to "macro" levels corresponds directly to a greatly increased risk of developing end-stage renal disease.

TABLE 1

Comparison of the Occurrence of NRIg to Albumin levels in the Urines of Diabetic Patients and in Patients with Hypertension

| Patients | Albumin level (ug/ml) | Type I Diabetics | | Type II Diabetics | | Hypertensive Patients[a] | |
|---|---|---|---|---|---|---|---|
| | | No. | NRIg+ | No. | NRIg+ | No. | NRIg+ |
| All | | 192 | 73/192 (38%) | 164 | 66/164 (40%) | 43 | 17/43 (40%) |
| Selected: | normal [<20] | 108 | 23/108 (21%) | 85 | 16/85 (19%) | 13 | 4/13 (31%) |
| | micro [20–200] | 55 | 23/55 (42%) | 62 | 34/62 (55%) | 24 | 8/24 (33%) |
| | macro [>200] | 29 | 27/29 (93%) | 17 | 16/17 (94%) | 6 | 5/6 (83%) |

[a]All hypertensive patients in this study had chronic hypertension for a minimum of 8 years duration. All were selected at random at a regular clinic visit.

Most importantly, elevated levels of NRIg in the urine of diabetic patients who received a kidney transplant correlate exactly with early signs of decreased renal function in the allograft, thereby being useful as a predictor of impending kidney failure and/or rejection.

NRIg occurs in the urine by a selective filtering mechanism(s) which is independent of the filtering mechanisms which permit albumin and total immunoglobulins (Ig) to appear in the urine; i.e., NRIg is actively transported from the blood into the filtering glomeruli of the kidney via specific receptors for the NRIg protein as opposed to being being present in the filtering glomeruli simply because damage or disease of the kidney permitted it to enter the urine unhindered. Therefore, because of selective filtration, urinary concentrations of NRIg do not correlate with the levels of NRIg found in serum from the same donor, nor do they correleate with the concentration of total (passively excreted) Ig's in the urine.

NRIg has been detected in immune complexes in the serum, as well as in the urine. However, detectable serum levels of the NRIg have not been useful in predicting the existence of kidney disease, as just mentioned above, whereas detectable levels of NRIg in the urine have been predictive of kidney disease.

Physical characteristics. NRIg is a unique human globular protein of molecular weight aproximately 150 kDa (range 140 kDa to 160 kDa), and is in the class of globular glycoproteins known as immunoglobulin G (IgG). It has been found in each of the several human IgG subtypes, including IgG1, IgG2, IgG3, and IgG4.

NRIg uniquely expresses antigenic determinants (epitopes) not expressed on other globular proteins (including other immunoglobulins). Therefore, NRIg is distinguished by its reactivity with a monoclonal antibody produced by ATCC hybridoma cell line deposit No. HB-10490, with a monoclonal antibody produced by ATCC hybridoma cell line deposit No. HB-10491, and with the equine-derived immune complex-binding RhC protein. As will be shown hereinafter, NRIg will bind any one of the foregoing reagents, or will simultaneously bind 2 or 3 of the foregoing reagents. Chemical reduction of NRIg causes unfolding of the NRIg molecule and results in the loss of binding with monoclonal IgG antibodies from the ATCC hybridoma cell line HB-10491; this indicates that these IgG monoclonal antibodies are binding to an epitope which is determined by the folding shape of the NRIg molecule. The binding of monoclonal IgM antibodies from the ATCC hybridoma cell line HB-10490 is not altered by such chemical reduction of NRIg.

NRIg is stable and can be measured in urine samples which have been stored frozen at −20° C. for at least 24 months.

Identification of NRIg. Western blots of urine from patients with kidney disease, probed with monoclonal antibodies produced by ATCC hybridoma cell lines No. HB10490 and No. HB-10491, showed a 150 kDa band that was also identified with commercial antihuman IgG antibodies (Fc and H and L chain specific), confirming the immunoglobulin nature of NRIg. Furthermore, protein-G affinity columns bound (i.e., captured) the nephropathy-related NRIg protein recognized by monoclonal antibodies from ATCC hybridoma cell lines No. HB-10490 and No. HB-10491. When the protein bound to the protein-G columns was selectively eluted, the eluates from these columns contained the 150 kDa protein, as detected on Western blots using the aforementioned monoclonal antibodies.

The hybridoma-derived monoclonal antibodies useful in the present invention are unique and took three years to develop. The murine hybridoma cell lines which produce these antibodies were obtained by the process discussed by G Kohler and C Milstein and reported in *Nature* 256: 495–497, 1975. The details of this process are well known in the art and will only be discussed briefly herebelow.

Hybridoma cell lines

In the process of the present invention, animals (preferably mice or rats) are immunized with a preparation containing NRIg protein; this can be either a preparation containing circulating immune complexes from serum, or a preparation of purified NRIg isolated from the urine of a patient who excretes high concentrations of NRIg. Five or more weeks subsequent to the first in vivo administration of NRIg immunogen the second dosage of immunogen is given. If the second dosage of antigen is administered sooner than approximately 3 weeks, the immunization response may be diminished in the animal.

Hybridomas producing monoclonal antibodies are generated by the somatic cell fusion of two cell types: 1) antibody-producing lymphocytes, called plasma cells, which are obtained from an immunized animal, and which, by themselves, can live for only a very short time in an artifical environment such as that of in a tissue; and 2) lymphoid tumor cells, called myeloma cells, which do not make antibodies but which have a capacity to grow very well and for "unlimited" periods of time is tissue culture medium. The myeloma cells used in the fusion process are cell-line variants which have been selected for a drug-sensitivity marker (such as a purine-synthesis enzyme deficiency) so that only those myeloma cells that have fused with normal antibody-producing plasma cells which provide the missing enzyme will survive under selective conditions of cell culture. The usual cell culture medium for selection of successfully fused cell hybrids is a medium containing the chemicals hypoxanthine, aminopterin, and thymidine (commonly called "HAT" medium). In this selective medium, unfused myeloma parent cells will die, unfused plasma cells will eventually die because of their short life span, and fused hybrid cells will grow indefinitely. Myeloma cell lines utilized for cell fusions are derived from a BALB/c mouse MOPC-21 myeloma as described by G Kohler and C Milstein (*Eur. J. Immunol.*, 6: 511–519, 1976). The myeloma cell line is identified as P3-NS1/1-Ag4-1. Fusion is brought about by mixing a suspension of the mononuclear cells containing antibody-producing plasma cells to the myeloma cells in culture medium and centrifuging the cell suspension to form a cell pellet. The cells in the pellet are then incubated in a growth medium containing the fusing agent, which can be polyethylene glycol. Suitable techniques for effecting fusion are described in the textbook by E Harlow and D Lane, entitled: *Antibodies: A Laboratory Manual*, New York: Cold Spring Harbor Laboratory, pp 139–243, 1988.

Hybridomas which synthesize and secrete antibodies directed solely toward determinants on the NRIg then are cultured to establish continuously proliferating cell lines with relatively stable genetic constitutions- The various cell lines obtained are cloned to ensure that the cells of the culture derived solely from a single cell. The cell lines or clones are propagated indefinitely in cell culture vessels or in vivo in syngeneic or immunodeficient hosts where said clones continue to synthesize and secrete monoclonal antibody to the NRIg antigens. Antibody is then recovered from the supernatant fluid of the cultured cells, or from the ascites fluids of histocompatable host animals by procedures which may involve conventional precipitation, ion exchange or affinity chromatography.

The hybridomas obtained by the present invention are capable of producing either IgM antibody or IgG antibody, the former being polyvalent. A cell line culture identified at the University of Nebraska Medical Center in Omaha as "TMDNM3" is on deposit with the American Type Culture Collection and is assigned ATCC accession number HB10490. This cell line produces a monoclonal antibody of the IgM isotype, which antibody reacts with high affinity with a determinant on the NRIg protein. Additionally, a cell line culture identified at the University of Nebraska Medical Center as "TMDNG2" is on deposit with the American Type Culture Collection in Rockville, Md., and is assigned the ATCC accession number HB-10491. This cell line produces monoclonal antibodies of the IgG1 isotype, which IgG antibody reacts with high affinity with a determinant on the NRIg protein.

In accordance with the present invention are provided hybridoma cell lines ATCC No. HB-10490 and No. HB-10491, and their progeny, whether derived directly (e.g., repeated daughter-cell derived cultures) or indirectly (e.g., any "second-generation" derived cultures, as defined hereinafter) from these hybridoma cell lines which are deposited with the American Type Culture Collection in Rockville, Md. Also in accordance with the present invention are provided any mRNA and any DNA molecules derived from the foregoing hybridoma cell lines and their progeny, and any genetically engineered products which might be derived from the use of these mRNA and/or DNA molecules. Such products would include but are not limited to any polyclonal or monoclonal antibodies and their antigen-binding fragments, and also any chimeric antibodies or antibody fragments which might be produced by use of these mRNA and/or DNA molecules in any genetic engineering process whatsoever, especially including processes involving use of a prokaryotic and/or eukaryotic host organism, or any combination of such host organisms, to produce the aforementioned polyclonal, monoclonal, or chimeric antibodies or antibody fragments. Exemplary of methods for the production of genetically-engineered antigen-binding antibody fragments are those disclosed in Huse et al., Science 246: 1275–1281, 1989.

By the term "chimeric antibody" is meant a genetically engineered antibody molecule in which different parts of the antibody molecule are coded for by genetic information obtained from at least two genetically different host organisms. For example, a chimeric antibody may be constructed by taking human genetic sequences which code for the structure of all but the antigen-combining site of an antibody molecule, and combining them with mouse genetic sequences which code only for the highly-specific antigen combining sites of the antibody molecule. The combined human/mouse genetic information will, when introduced into an appropriate and living host organism, direct that living organism to make the genetically engineered chimeric antibody.

By "indirect" derivation of progeny is meant any process which uses monoclonal antibodies (e.g., those produced by the ATCC hybridoma cell lines HB-10490 and/or HB-10491) to isolate, by any of a variety of conventional antigen-binding affinity procedures, the NRIg protein from new samples of NRIg-containing body fluids, such as patient-derived urine, and using the freshly-isolated NRIg as an immunogen in animals for generating either a) polyclonal antibodies specific for the NRIg, and/or b) immune lymphocytes useful in the development of new (or "second-generation") hybridoma cell lines which can be used to produce new monoclonal antibodies specific for antigenic determinants on NRIg.

It is the intent of this application to cover all hybridoma antibody producing cell lines derived from ATCC hybridoma cell line No. HB-10490 or from ATCC hybridoma cell line No. HB-10491, whether developed by culturing and subcloning of progeny directly from the ATCC cell line, or by preparing "second generation" hybridomas as discussed above, or by genetic engineering procedures as described above.

Monoclonal Antibodies

The immunogenic NRIg glycoprotein of the present invention expresses unique immunogenic determinants which are useful in inducing the production of polyclonal and monoclonal antibodies. Such antibodies are then useful for binding specifically to those antigenic determinants.

In one embodiment of the present invention, there is provided a set of monoclonal antibodies comprising two antibodies of differing isotypes which exhibit a specificity of binding which is solely directed against antigenic determinants on the human nephropathy-related globular protein (NRIg) of this invention. One antibody of the set is a macroglobulin antibody of an immunoglobulin M (IgM) isotype. This antibody is pentomeric, having 5 pairs of anti-NRIg combining sites (total of 10 antigen binding sites) per molecule, and is produced by ATCC hybridoma cell line deposit No. HB-10490. Another antibody of the set is an antibody of the immunoglobulin G (IgG) isotype which has one pair of anti-NRIg combining sites (total of 2 antigen binding sites) per molecule. This IgG monoclonal antibody is produced by ATCC hybridoma cell line deposit No. HB10491.

The aforementioned monoclonal antibodies bind to NRIg with very high affinity, i.e., with a binding affinity constant of at least $10^9$ liters/mole. The terms "high affinity" and "a binding affinity constant of at least $10^9$ liters/mole" are used interchangeably. Although the affinity constant for this immunoreactive binding has not yet been directly measured, it is known to be very high, since any immune complex formed by the binding of NRIg protein and either of the aforementioned monoclonal antibodies must be exposed to nearly denaturing conditions in order for there to be substantial separation of the monoclonal antibody and the NRIg.

Given the availability of the high-affinity antibody-producing repository cell lines of the present invention, it is obvious to anyone skilled in the art that new and equivalent antibodies to the protein of the present invention can be prepared by procedures which involve a process called "antibody xeroxing," which process is also known as preparation of "second-generation" antibodies (Muraro et al., *Cancer Research* 48:4588–4596, 1988). It is the intent of this application, therefore, to cover all polyclonal and monoclonal antibodies which are derived either directly or indirectly (as previously defined herein) from ATCC hybridoma cell line No. HB-10490, or from ATCC hybridoma cell line No. HB-10491.

Isolation of "second-generation" antibodies to NRIg involves immunological procedures substantially equivalent to the following:

1. Binding of antibody derived directly or indirectly from one of the ATCC cultures mentioned above to an inert substrate, thereby immobilizing the antibody on that substrate and making an affinity matrix which is used to capture and isolate NRIg from a biological solution suspected of containing the NRIg, such as urine from a patient with nephropathy;
2. Incubation of the NRIg-containing biological fluid with the antibody-coated substrate. During this incubation, NRIg is specifically adsorbed onto the affinity matrix and remains firmly bound to the immobilized antibody. Any and all unbound proteins are easily washed away from the antibody-coated substrate, leaving only the NRIg protein bound to the affinity matrix;
3. Elution of the NRIg from the affinity matrix, after which it is concentrated by standard laboratory procedures, and injected into another host (such as a mouse or rat) by standard procedures used for animal immunization;
4. Isolation of antibody-producing plasma cells from the spleen of such an immunized animal host (such as from a mouse or rat) and fusion of these plasma cells with "immortal" myeloma tumor cells, using standard fusion procedures for production of hybridomas;
5. Detection and cloning of hybridoma cell cultures which produce monoclonal antibodies directed against antigenic determinants on NRIg. These newly derived hybridoma clones secrete monoclonal antibodies which are designated "second-generation" monoclonal antibodies, and these antibodies should be substantially equivalent to the antibodies produced by ATCC hybridoma cell lines HB-10490 and HB-10491 in their specificity for binding antigens on NRIg.

Assays for NRIg

As shown by the following examples, NRIg has been detected in samples of body fluids in a number of different assays, which include dual antibody sandwich EIA assays, an EIA which used RhC instead of monoclonal antibody to capture NRIg, and radial immunodiffusion (RID) assays. In these examples, the description of reagents as being percentages in solution are meant to indicate weight of reagent per volume of solution (e.g., a 1% solution equals 1 gm of reagent per 100 ml of solvent), unless otherwise stated.

EXAMPLE 1

The Isolation of the NRIg nephropathy-related protein from body fluids and the production of monoclonal antibodies to NRIg.

The following example demonstrates how the novel NRIg protein of the present invention was identified, and subsequently isolated from a selected body fluid such as serum of individuals who had renal disease. It also demonstrates how the unique monoclonal antibodies of the present invention were developed.

Because NRIg is itself an immunogenic molecule, it was first isolated as a constituent of circulating immune complexes (CIC) found in the blood serum of patients who had end-stage renal disease. Blood serum was obtained from each of 16 individual patients who were on renal dialysis; ten Type I and six Type II diabetic patients were included in this study without distinction. All had been on renal dialysis for no more than 2 years, and all had elevated levels of immmune complexes in their sera (ranging from a low of 5 times normal values to 20 times normal). CIC were isolated by the solid phase method of RhC, and all isolated complexes from a given patient were pooled into one container and frozen. Similarly, CIC from the sera of 16 "control" individuals who either had a disease completely unrelated to diabetes, or who were normal, healthy individuals, were isolated by the solid phase RhC method and individually pooled and frozen as above.

The solid phase RhC method mentioned above to isolate these complexes was done essentially as follows: RhC immune complex-capturing protein was solubilized in a TRIS buffer, pH 8, and immobilized onto the flat plastic surface of each of the wells of a 6-well culture plate, each well being approximately 35 mm in diameter and 12 mm deep (Falcon Plastics No. 3046, from Becton Dickinson Labware, Lincoln Park, N.J.). Five ml of serum from each individual patient (whether diabetic or a "control") were diluted 1:5 in TRIS/Tween buffer, pH 8 (i.e., 5 ml serum+20 ml buffer), and 1 ml of each diluted serum sample was plated into a separate RhC-coated well, for a total of 25 wells utilized per individual donor (5 plates per patient). After incubation in a humidified chamber at 37° C. for 1 hr, the diluted serum was decanted from each well, and the wells were washed repeatedly with TRIS/Tween buffer to remove any unbound protein, leaving only CIC bound to the RhC on the plates.

The serum-derived CIC which had been captured by the RhC on the plastic were then eluted with 0.5 ml of 0.1% acetic acid in water, for 15 min at 37° C. Alternately, 4M urea containing 0.1% sodium dodecylsulfate (SDS) was used to elute the bound CIC for the same time and temperature. The CIC eluted from each of the 25 wells from a given donor were then pooled and concentrated by dialysis with an Amicon filter which had a 2000 molecular weight cutoff (Amicon Corporation, Beverly, Mass. 01915). The pooled, concentrated CIC from each donor was then frozen until used.

To specifically identify and isolate the antigen from the mixture of CIC, it was decided to make antibodies which could be used as affinity reagents for a potential nephropathy-related protein. In order to make the antibodies specific to an antigen in the complexes obtained from diabetic patients, it was planned to first tolerize animal hosts with immune complexes isolated from control, non-diabetic donors, thereby tolerizing the mice to common constituents that occur in all immune complexes. To do this, aliquots of CIC from 16 control, non-diabetic donors were separately thawed and then pooled into one suspension; exactly 100 ug of protein from this pool of control CIC were injected into the peritoneal cavity (abdominal region) of five BALB/c mice on day 0. Twenty-four hours later (on day 1), the immunized animals were given an injection of cyclophosphamide, a chemical which binds to and kills any immune lymphocytes which were activated by exposure to the control CIC. Cyclophosphamide (at 50 ug/kg of body weight) was also given on day 3, and again on day 5, to ensure that all lymphocytes activated by exposure to the control CIC were eliminated from the host animal.

After resting the animals for 3 weeks, these tolerized animals were then immunized with the CIC from the diabetic individuals. No adsorptions to remove so-called "normal" proteins from the diabetic CIC pool were performed prior to the use of those complexes in animal immunization, since it was important not to bias the results by "preselecting" what was defined as "normal" and what was "not normal" in this material. Aliquots of CIC from all 16 diabetic patients were pooled, and exactly 200 ug of this pooled CIC mixture were injected together with complete Freund's adjuvant subcutaneously at the back of the neck of each animal. Two weeks later, these animals were boosted with exactly 100 ug of diabetic CIC in incomplete Freund's adjuvant. Seven days later, the animals were sacrificed and their spleens were used in a standard hybridoma fusion process of G Kohler and C Milstein (*Nature* 256: 495–497, 1975).

The screening of hybrids produced as a result of the fusion was designed to identify positive hybrids by their reactivity on EIA plates coated with urinary proteins from 6 diabetic patients who had clinically-confirmed nephropathy, as determined by their having persistent macroproteinuria in the range of 1+ to 2+ on "Albustix" dipstick assay (i.e., in the range of 300 ug/ml to 1 mg/ml of protein in their urine). The EIA plates had been coated in standard fashion, using a final concentration of 1 ug urinary protein per well in pH 9.6 bicarbonate buffer. The negative screen was set up using EIA plates coated in a similar manner using urines from 7 control patients whose nephropathy was not related to diabetes (4 patients had chemically-induced nephropathy due to cisplatimun treatment for breast carcinoma, and 3 had glomerulonephritis due to Lupus).

After screening more than 8000 separate hybridoma producing wells, which were developed after 5 separate fusion experiments, a total of 12 mixed hybrid cultures, which exhibited reactivity with the diabetic CIC-coated EIA wells but not with the control CIC-coated EIA wells, were selected and frozen in anticipation of further study and cloning. Four of these cultures which exhibited the highest degree of specificity for the diabetic over control CIC were subsequently cloned by standard procedures of limitingdilution analysis. More than 4000 separate screening tests were performed on cloned hybrids obtained from the four mixed hybrid cultures, and, from those studies, 2 hybridoma cell lines were selected which produced monoclonal antibodies which exhibited high-affinity binding with the diabetic-derived CIC and no binding to the control CIC. One of these hybridomas produced an IgM antibody and the other produced an IgG1 antibody. The specific target antigen in the molecular structure of the pooled diabetic-derived CIC to which these monoclonal antibodies were directed was still not known.

The multitude of proteins in the urines from diabetic patients with kidney disease were physically separated by electrophoresis on polyacrylamide gels and then probed with both of the antibodies, in a process called Western blotting. The antibodies identified a band on the gels which had a molecular weight of approximately 150,000 daltons that was also specifically identified with commercial antihuman IgG antibodies (Fc and H & L chain specific). Furthermore, Protein-G affinity columns, to which only immunoglobulin G molecules will adhere, captured from diabetic urines the protein recognized by both monoclonal antibodies. Lastly, eluates from these Protein-G columns contained the 150 kDa protein detected with the monoclonal antibodies on Western blots.

EXAMPLE 2

Making polyclonal antibodies to the NRIg nephropathy-related protein of the present invention When an immunogenic substance is introduced into a living host, the host's immune system responds by producing antibodies to all of the recognizable sites on the substance. Many different antibody-producing cells from many different places in the host's body will be making antibodies to that part of the immunogenic substance by which they were activated; each antibody-producing clone making only one type of antibody to only one antigenic epitope on the foreign substance. This very broad response by the immunized host which results in the production of a broad range of antibodies of differing affinities and specificities for the immunogenic substance is called a polyclonal antibody response.

There are situations in which immunometric assays for NRIg may be more effectively carried out with polyclonal antibodies than with hybridoma-produced monoclonal antibodies, such as in radial immunodiffusion (RID) assays in which immunoprecipitation of the target antigen is required. The following prophetic examples illustrate how polyclonal antibodies can be raised, either in rabbits or in chickens, against the NRIg nephropathy-related protein of the present invention.

Rabbits as host. Purified NRIg obtained using the procedures outlined in Example 1 above is prepared as a solution of 400 ug protein in 0.8 ml of phosphate-buffered saline, pH 7.2, and mixed thoroughly with an equal volume of complete Freund's adjuvant (Difco, Detroit, Mich.), and sonicated until a homogeneous milky-white suspension is obtained. Using a 1-ml syringe equipped with a 23-gauge needle, equal volumes of 0.2 ml are injected into the muscle mass at the top of each leg of a large New Zealand white rabbit. This process is repeated 3 more times; the first booster 2 weeks later, and the second and third booster inoculations following at 4-week intervals, using the same amount of NRIg in the first booster inoculation, and half the amount of antigen in the second and third booster injections. Each of these booster inoculations is prepared in incomplete Freund's adjuvant, in order to avoid inducing a hypersensitive shock reaction to the adjuvant used, and to prevent formation of granulomas at the site of intramuscular injection.

In order to monitor the progress of the immunization procedure, blood samples are taken from the host rabbit just prior to the start of immunization (from this is obtained the control, background serum sample), and then just prior to each immunization in this schedule.

After the third booster injection (given at the beginning of week 10 of the immunization protocol), the animal is rested for an additional 4 to 8 weeks, during which time the antibody response of the host rabbit is maturing into one which is primarily producing IgG antibodies. Furthermore, the affinity of the IgG antibodies being produced is increasing significantly as the number of booster injections continue, and as the time after the initial immunization exposure increases. At week 14 of the immunization schedule, then, the immunized rabbit is bled to obtain a serum sample for testing and is then given booster inoculations of NRIg (100 ug antigen distributed equally between the four injection sites) in incomplete Freund's adjuvant. One week later, 50 ml of blood is taken from the marginal ear vein of the animal to provide a volume of approximately 25 ml of immune serum containing high concentrations of high affinity IgG antibodies directed against the NRIg protein of this invention. With care, this much blood can be taken monthly from the same donor animal as long as is necessary.

The rabbit polyclonal antibodies prepared in this way not only have a high binding affinity for antigenic sites on the human NRIg protein of the present invention, but they also have—due to their polyclonal derivation—a high binding affinity for many antigenic sites common to all human IgG antibody molecules which are found in human tissues and body fluids. In order to make the polyclonal rabbit antiserum specific for antigens unique to the NRIg protein, it is necessary to remove antibodies to as many of the common antigens as is possible. To do this, the rabbit polyclonal antiserum is filtered by column chromatography through an affinity column to which is bound human polyclonal immunoglobulins (such as human Cohn Fraction II, Sigma Chemical Company, St. Louis, Mo.). The rabbit antibodies to the common antigens found on human immunoglobulin molecules will remain bound to the column, while antibodies to unique antigenic epitopes on NRIg will pass through the column and be collected in the eluate, which is then concentrated by dialysis with an Amicon ultrafilter with a molecular weight cutoff of 2000. This affinity chromatography process is repeated until the rabbit polyclonal antiserum no longer reacts with normal human IgG preparations (such as Cohn Fraction II) but continues to react with NRIg in EIA assays. At this point, the polyclonal antiserum is again concentrated by Amicon ultrafiltration, and is then tested to determine the concentration and affinity of the remaining anti-NRIg antibodies.

Chickens as host. The use of chickens as an alternative source of polyclonal antibodies to mammalian proteins has been described (Polson et al., *Immunological Communications* 9: 495–514, 1980; Gassman et al., *FASEB Journal* 4: 2528–2532, 1990). After immunization, polyclonal antibodies are found at high concentrations in the yolk of the avian host. An advantage of using chickens as a source of specific antibody, according to Gassman et al., is that the amount of antibody produced in the chicken in one month can be about 18 times higher than that produced in a rabbit.

From 20–30 ug of mammalian protein are sufficient to induce an excellent immune response in the chicken. The NRIg antigen is diluted in 0.01M potassium phosphate buffer (pH 7.2) containing 0.1M NaCl to a final volume of 750 ul and emulsified by sonification with an equal volume of complete Freund's adjuvant (Difco, Detroit, Mich.). The thoroughly mixed suspension (1.5 ml) is injected at two sites into the pectoral muscle of a brown Warren or white Leghorn egg-laying hen. Additional injections of the NRIg protein, emulsified as described above with complete Freund's adjuvant, are given to the hens on day 12 and day 20 after the first injection. The eggs of the immunized hosts are collected daily, marked and stored at 4° C. until used.

Specific anti-NRIg antibodies should appear in the egg yolks approximately 20 days after immunization, reach a plateau after 30 days, and remain high until at least day 81. Several grams of immunoglobulin may be extracted from as many as 60 eggs from one immunized hen. To isolate specific anti-NRIg antibodies from egg yolk immunoglobulins, purified NRIg is conjugated to CNBr-activated Sepharose 4B (0.2 mg proein per column) according to the manufacturer's instructions (Pharmacia, Piscataway, N.J.). The column (0.5 ml) is loaded with 10 mg of of purified chicken egg yolk immunoglobulin (isolated exactly as reported by Gassman et al) and eluted according to manufacturer's instructions. Approximately 100 to 130 mg of specific antibody may be obtained from several grams of chicken egg yolk immunoglobulin.

EXAMPLE 3

Ability of monoclonal antibodies to capture and identify NRIg in an Enzyme-Linked Immunosorbant Assay (EIA)

The following example demonstrates that monoclonal antibodies produced by ATCC hybridoma cell line No. HB-10490 and bound to a solid matrix were able to capture NRIg from a small volume of urine, and that monoclonal antibodies produced by ATCC hybridoma cell line No. HB-10491 and labeled with an enzyme marker were able to identify with specificity, in a sandwich-type EIA assay, the NRIg which had bound to the first antibody.

EIA assay plates. The preferred assay plates used for this EIA were 96-well "Immulon-2" microtest plates, with flat-bottomed wells, manufactured by Dynatech (Dynatech Laboratories, Inc., Chantilly, Va.).

Monoclonal antibodies. Two monoclonal antibodies were raised in a murine host against unique antigenic determinants expressed on purified NRIg protein. One monoclonal antibody was of the macroglobulin IgM isotype, and was produced by the hybridoma cell line which has the ATCC deposit No. 10490; the second monoclonal antibody was of the gamma globulin IgG isotype, and was produced by the hhybridoma cell line which has the ATCC deposit No. 10491. Both antibodies bind the NRIg target molecule with very high affinity (i.e.,$>10^9$ liters/mole), and apparently recognize different epitopes on the same molecule.

Carbonate/Bicarbonate coating buffer. This buffer, which contains sodium bicarbonate to a final concentration of 0.015M, and also contains monosodium carbonate to a final concentration of 0.035M, was prepared as follows: 0.78 grams of sodium bicarbonate and 1.46 grams of monosodium carbonate were added to 500 ml of deionized water. The pH of the final solution is 9.6.

PBS/Tween-20 buffer. Non-specific interactions between proteins are prevented when a buffer solution containing a mild detergent is used in the washing steps of the EIA assay. This buffer contains the following final concentrations of reagents: 0.002M monosodium phosphate, 0.008M disodium phosphate (anhydrous), 0.15M sodium chloride, and 0.05% Tween-20 detergent. This buffer was prepared by mixing 0.28 g monosodium phosphate, 1.13 g disodium phosphate (anhydrous), 8.77 g sodium chloride, and 0.5 ml of Tween-20 in one liter of deionized water. After thorough mixing to dissolve all of the salts, the pH was adjusted to neutrality (pH 7.0–7.2).

Diethanolamine buffer. 97 ml of diethanolamine, and 100 mg magnesium chloride were added to 800 ml deionized water. To this were added drops of 1M hydrochloric acid until the pH reached 9.8, after which deionized water was added to a final volume of 1 liter. This light-sensitive buffer was stored in the dark at 4° C. until used.

Phosphatase substrate for the assay. Paranitrophenyl phosphate, disodium salt, was obtained as 5 mg tablets from Sigma Chemical Corporation, St Louis, Mo. (Sigma. 104 Phosphatase Substrate Tablets). To prepare this substrate for use, one phosphatase substrate tablet was thoroughly dissolved in 5 ml of cold diethanolamine buffer, with occasional gentle mixing, in the dark. After the tablet was fully dissolved, the solution was warmed to room temperature just before use.

Alkaline phosphatase-conjugated antibodies. Alkaline phospatase-conjugated goat IgG antibodies with binding directed specifically against the Fc fragment of mouse IgG were purchased from Jackson ImmunoResearch Laboratories, Inc., West Grove, Pa.).

EIA Assay procedure. Monoclonal antibodies from ATCC cell line HB-10490 were purified from hybridoma tissue culture fluid by using the Bakerbond ABx Batch Extraction Protocol (pages 121–123 of the JT Baker Products for Chromatography catalog, 1988–89; JT Baker Company, Phillipsburg, N.J.). The ABx matrix used was the 40 micrometer size (designated 40-um "Prepscale" ABx). The monoclonal antibody was diluted to 10 ug/ml in carbonate/bicarbonate buffer. Alternatively, the IgM antibodies from HB-10490 were purified from ascites fluid by precipitation in a 40% ammonium sulfate solution, followed by dialysis against phosphate-buffered saline (PBS). The dialyzed solution was then passed over a protein-G column (Genex Incorporated, Gaithersburg, Md.) to remove any contaminating murine IgG molecules contained in the ascites fluid. The column eluate was then collected and diluted to 1 ug/ml in carbonate/bicarbonate coating buffer.

One hundred ul of diluted antibodies from HB-10490 were added to each well of an EIA plate, and the plate was covered and incubated at 37° C. After 2 hr, the plate was removed from the incubator and was either used immediately or was stored at room temperature for up to 2 days before use. The wells of the plate were washed twice (2X) for 5 min each with PBS/Tween buffer.

To each well of the EIA plate, 100 ul of PBS/Tween buffer were added, followed by 25 ul of urine specimens, into separate and appropriate wells. Each specimen was tested in triplicate replicates. The solutions in the wells were mixed by gently tapping the plate several times, the plate was covered, and was incubated at 37° C. After 1.5 hr at 37° C., the plate was washed twice (2X) with PBS/Tween-20 buffer, for 5 minutes per wash.

Monoclonal antibodies from the hybridoma cell line ATCC No. HB-10491 were purified by the Bakerbond ABx Batch Extraction Protocol (JT Baker Company) and diluted to 2.5–3.0 ug/ml in PBS/Tween buffer, as determined by standard radial immunodiffusion analysis (as outlined in N Rose, H Friedman and J Fahey, *Manual of Clinical Laboratory Immunology*, 3rd edition, Washington D.C.: American Society of Microbiology Press,pp.17–19, 1986). One hundred ul of this IgG antibody were added to each well of the EIA plate, the plate was covered, and then incubated for 1 hr at 37° C. The plate was again washed twice, for 5 minutes for each wash, using PBS/Tween buffer as the wash solution.

An enzyme-conjugated goat anti-mouse antibody was diluted 1:5000 in PBS/Tween buffer, and 100 ul were added to each well of the EIA plate, after which the plate was covered and incubated for 1 hr at 37° C. The plate was again washed twice, for 5 min each, with PBS/Tween buffer. To each well were then added 100 ul of freshly prepared substrate (3,3'-diaminobenzidine), followed by incubation for exactly 1 hr at 37° C.

The amount of color development in each well, which was proportional to the amount of enzyme-conjugated goat anti-mouse antibody which bound to the second antibodies in the wells, was quantitated by scanning the plate in an automated spectrophotometer called an "EIA plate reader", set at an absorbance wavelength of 405 nm (Dynatech Laboratories, Chantilly, Va.). The optical density (O.D.) reading printed out for each individual well was a number which was directly proportional to the amount of light absorbed by the sample solution in that well; i.e., the higher the O.D. reading, the greater the amount of light that was absorbed by the fluid in the well being analyzed. Furthermore, the amount of light absorbed in a well was directly proportional to the amount of NRIg which was originally bound in that well. Therefore, the higher the OD reading for a well, the higher the amount of NRIg in that sample of body fluid.

As shown in Table 2, the range of EIA O.D. measurements in urines from patients and from healthy individuals was dramatic. For example, the urines of normal, healthy individuals had an O.D. range that did not exceed a low reading of 0.200, whereas the urines from patients suffering with advanced end-stage renal disease had very high O.D. readings ranging from 2,500 to 3,000. In between, patients with varying stages of nephropathy (as defined by the existence of clinically detectable protein in their urine) had EIA O.D. readings which ranged from 0.220 to 2.750. Therefore, a positive reading in the EIA for NRIg was determined to be any O.D. measurement which exceeded 0.200.

TABLE 2

Parameters of EIA for Detection of NRIg

| Urine (1:5 dilution) | n | EIA (O.D. at 405 nM) |
|---|---|---|
| Normal | 37 | 0.14 ± 0.05[a] |
| ESRD | 22 | 2.50 ± 3.00 (CV < 5%) |
| Nephropathy | 25 | range 0.22 ± 2.75 (CV < 15%) |

NRIg positive EIA defined as O.D. > 0.200.
[a]O.D. = mean value in arbitrary units from specimens assayed in triplicate.

Having determined what constituted a positive assay for NRIg, it was important to determine the frequency with which this NRIg protein occurred in the urines of individuals who had clinically-confirmed nephropathy. As shown in Table 3, for 33 diabetic patients with established nephropathy or end-stage renal disease (ESRD), NRIg was detectable at elevated levels in 100% of the urines.

Because the nephropathy-related NRIg protein of the present invention is an immunoglobulin of the IgG isotype, it was important to determine the frequency with which the common IgG serum protein could be found in urine specimens, and, once that was done, to determine whether the presence of the nephropathy-related NRIg protein correlated in any way with the presence of this broader category of IgG in urines from patients with clinically-confirmed nephropathy.

TABLE 3

Occurrence of NRIg in Diabetic Patients with Established Nephropathy[a] or End-Stage Renal Disease (ESRD)

| Patient Stage | Type I | Type II | NRIg+ |
|---|---|---|---|
| Nephropathy | 10 | 7 | 17/17 (100%) |
| ESRD | 11 | 5 | 16/16 (100%) |

[a]Long-standing diabetes, macroproteinuria, elevated serum creatinine, elevated blood urea nitrogen (BUN).

According to the data in Table 4, immunoglobulin IgG was present in the urines of 79 of the 192 Type I diabetic patients tested (=41%), and in the urines of 50 of the 164 Type II diabetic individuals tested (=30%). When a single nephropathy-related risk factor such as the amount of albumin present in the urine (which should be a direct indicator of the level of kidney disease) was also factored into the evaluation of urine samples, the data in Table 4 indicated that the more advanced the nephropathy (as shown by higher levels of albumin in the urine) the more commonly was IgG simultaneously found in those urine samples. It should be noted, however, that even in cases of extreme proteinuria (>200 ug albumin per ml of urine), only 66% of the patients had elevated levels of IgG (i.e., greater than 4 ug/ml) in their urine. Therefore, by itself, the presence of IgG in urine is not a useful indicator of the presence or degree of nephropathy.

TABLE 4

The occurrence of IgG in urine specimens with different levels of albumin

| Patients | Albumin level (ug/ml) | Type I Diabetes No. | IgG+[a] | Type II Diabetes No. | IgG+ |
|---|---|---|---|---|---|
| All | <20 to >200 | 192 | 79/192 (41%) | 164 | 50/164 (30%) |
| Categories: | Normal (<20) | 108 | 32/108 (30%) | 85 | 12/85 (14%) |
| | Micro (20–200) | 55 | 28/55 (51%) | 62 | 27/62 (44%) |
| | Macro (>200) | 29 | 19/29 (66%) | 17 | 11/17 (65%) |

[a]Urines were considered to be positive for IgG when IgG concentrations were greater than 4 ug/ml.

Because NRIg is in the class of IgG molecules, it was important to determine how many of the IgG-positive urine examples represented in Table 4 simultaneously contained detectable levels of NRIg. According to the EIA data in Table 5, approximately half of the 79 Type I and Type II patients with IgG in their urine also had NRIg in their urine. When, however, these IgG-positive urine specimens were categorized according to the additional nephropathy-related risk factor of levels of albumin they also contained, a very dramatic observation was made: more than of all Type I and Type II diabetics with macroalbuminuria also had NRIg in their urine.

TABLE 5

The occurrence of NRIg in IgG-positive urine specimens with different levels of albumin

| Patients | Albumin level (ug/ml) | Type I Diabetes No. | NRIg | Type II Diabetes No. | NRIg |
|---|---|---|---|---|---|
| All | <20->200 | 79 | 40/79 (51%) | 50 | 27/50 (54%) |
| Categories: | normal (<20) | 32 | 8/32 (25%) | 12 | 2/12 (17%) |
| | micro (20–200) | 28 | 14/28 (50%) | 27 | 15/27 (56%) |
| | macro (>200) | 19 | 18/19 (95%) | 11 | 10/11 (91%) |

Unexpectedly, elevated levels of NRIg were also found in the urine of approximately 20% of diabetics who were without clinical laboratory evidence of kidney disease or microalbuminuria (range, 25% of Type I and 17% of Type II diabetics); the appearance of NRIg in these patients appeared to indicate that clinically-undetectable incipient nephropathy was present. This was supported by data which showed that as the level of albumin in the urine of patients increased from normal low levels to macro levels, the percentage of patients with NRIg in their urine also dramatically increased, exactly in parallel with the increase in risk of end-stage renal disease. NRIg appeared then, to be a valuable predictor of impending development of overt kidney disease. The distribution frequency of NRIg in Type I and Type II diabetic patients, and in patients with hypertension, at different levels of albuminuria is summarized in Table 6, where the increase in albuminuria from normal levels to "macro" levels corresponds directly to a greatly increased risk of developing end-stage renal disease.

TABLE 6

Comparison of the Occurrence of NRIg to Albumin levels in the
Urines of Diabetic Patients and in Patients with Hypertension

| Patients | Albumin level (ug/ml) | Type I Diabetics No. | Type I Diabetics NRIg+ | Type II Diabetics No. | Type II Diabetics NRIg+ | Hypertensive Patients[a] No. | Hypertensive Patients[a] NRIg+ |
|---|---|---|---|---|---|---|---|
| All | | 192 | 73/192 (38%) | 164 | 66/164 (40%) | 43 | 17/43 (40%) |
| Selected: | normal [<20] | 108 | 23/108 (21%) | 85 | 16/85 (19%) | 13 | 4/13 (31%) |
| | micro [20–200] | 55 | 23/55 (42%) | 62 | 34/62 (55%) | 24 | 8/24 (33%) |
| | macro [>200] | 29 | 27/29 (93%) | 17 | 16/17 (94%) | 6 | 5/6 (83%) |

[a]All hypertensive patients in this study had chronic hypertension for a minimum of 8 years duration. All were selected at random at a regular clinic visit.

These data indicate that when the presence of NRIg in the urine was measured simultaneously with only one additional risk factor, such as the degree of albuminuria, the NRIg became a very useful indicator of the degree of nephropathy in that individual.

A very important risk factor in diabetes which predisposes the patient to nephropathy is the length of time that that patient has had diabetes. The occurrence of NRIg is Type I diabetic patients was compared to the duration of disease, and also compared to the amount of albumin present in the urines. This is important since it is known that the clinical evidence of kidney disease in diabetic patients typically occurs after about 15 years duration of diabetes and that microalbuminuria places the patient into a high risk group for developing end stage renal disease. As shown in Table 7, the frequency of NRIg-positive patients increased with the duration of diabetes regardless of the level of proteinuria. In the diabetic patient group who had microalbuminuria, the frequency of NRIg increased from 14% for those who had a duration of less than 5 years to almost 60% after 15–20 years of having had the disease.

progress to microalbuminuria and eventually to end-stage renal disease. However, the data available to date indicate that the occurrence of NRIg in the urine is a marker of kidney disease and its prevalence in the diabetic population is in agreement with results for a nephropathy-related "marker protein" expected from epidemiological morbidity studies.

These data are summarized in the graph in FIG. 1. The solid line represents the frequency of albuminuria at different durations of diabetes as predicted from epidemiological studies. The graph illustrates that between 10–15 years duration, approximately 50–60% of all Type I diabetics will develop microalbuminuria. Of those patients who do develop microalbuminuria, approximately 70% will continue to progress toward more advanced nephropathy, which would be characterized by much higher levels of albumin being excreted in the urine (macroalbuminuria). Unfortunately, 90% of the patients who have had diabetes for 15–20 years and who have developed macroalbuminuria will develop end-stage renal disease. The frequencies of NRIg in the Type I diabetics in this study at different durations of

TABLE 7

Comparison of the Occurrence of NRIg with the Duration
of Type I Diabetes in 192 Patients at Different Levels of Albuminuria

| Patients | Albumin level (ug/ml) | No. of NRIg+ patients | Duration (years) 1–5 | 6–10 | 11–20 | >20 |
|---|---|---|---|---|---|---|
| All | <20–>200 | 73/192 | 24 | 29 | 77 | 62 |
| Selected: | normal (<20) | 23/108 (21%) | 3/17 (18%) | 8/19 (42%) | 10/44 (22%) | 2/28 (7%) |
| | micro (20–200) | 23/55 (42%) | 1/7 (14%) | 3/8 (37%) | 9/22 (41%) | 10/18 (56%) |
| | macro (>200) | 27/29 (93%) | none | 2/2 (100%) | 9/11 (82%) | 16/16 (100%) |

The highest percentage of NRIg-positive diabetics who did not have albumin in their urine occurred in those patients with a duration of disease of only 6–10 years. The frequency of NRIg decreased to only 7% of the 28 patients who did not develop proteinuria even after 20 years of having diabetes; diabetics in this category are known to have a low incidence of kidney problems. The low incidence of NRIg-positive urines in this group is consistent with this latter point. There is insufficient data at this time to prove that the NRIg-positive patients who have normal urinary albumin will diabetes and at different levels of proteinuria are shown in FIG. 1 by the hatched bars. The numbers at the top of the bars show the percentage of NRIg-positive patients at a given duration as kidney disease progresses. The data showing the occurrence of NRIg in Type II diabetic patients, compared to the duration of their diabetes, is similar to that shown above for Type I patients and is presented in Table 8.

TABLE 8

Comparison of the Occurrence of NRIg with the Duration of Type II Diabetes in 164 Patients at Different Levels of Albuminuria

| Patients | Albumin level (ug/ml) | No. of NRIg+ patients | Duration (years) | | | |
| --- | --- | --- | --- | --- | --- | --- |
| | | | 1–5 | 6–10 | 11–20 | >20 |
| All Selected: | <20–>200 | 66/164 | 55 | 46 | 44 | 19 |
| | normal (<20) | 16/85 (19%) | 6/38 (16%) | 5/23 (22%) | 5/17 (30%) | 0/7 (0%) |
| | micro (20–200) | 34/62 (55%) | 8/14 (57%) | 12/20 (60%) | 13/20 (65%) | 1/8 (13%) |
| | macro (>200) | 16/17 (94%) | 3/3 (100%) | 3/3 (100%) | 6/7 (86%) | 4/4 (100%) |

When several factors related to kidney function were simultaneously considered, the correlation between the presence of NRIg in urine and the presence of nephropathy became extremely strong. For example, when levels of serum creatinine were considered in addition to the presence of albumin in urine, the data in Table 9 were obtained:

TABLE 9

Comparison of the occurrence of NRIg to serum creatinine in patients with different levels of albumin

| Patient Characteristics | Type I | | Type II | | Hypertensive | | NRIg+ Total |
| --- | --- | --- | --- | --- | --- | --- | --- |
| | No. | NRIg+ | No. | NRIg+ | No. | NRIg+ | |
| All patients | 145 | | 111 | | 38 | | |
| Creatinine >1.4 mg/dl | 16 | 13/16 | 19 | 12/19 | 8 | 7/8 | 32/43 (74%) |
| Albumin (ug/ml) | | | | | | | |
| Normal (<20) | 3 | 0/3 | 6[a] | 1/6 | 2 | 1/2 | 2/11 (18%) |
| Micro (20–200) | 3 | 3/3 | 6 | 4/6 | 3 | 3/3 | 10/12 (83%) |
| Macro (>200) | 10 | 10/10 | 7 | 7/7 | 3 | 3/3 | 20/20 (100%) |

[a]Five NRIg-negative patients, two were receiving chemotherapy for cancer

It is possible, and even desireable, to analyze simultaneously three or more factors related to kidney function, such as levels of creatinine in the serum, levels of albumin in the urine, and whether or not the patient is experiencing hypertension. By assessing and correlating these factors together with information on the amount of NRIg which is found in the patient's urine, a dramatic association between these high risk factors was found, as is shown in Table 10:

TABLE 10

Frequency of NRIg in diabetic patients with multiple risk factors for nephropathy

| Patients included | Risk Factors considered | Type I Diabetics | | Type II Diabetics | |
| --- | --- | --- | --- | --- | --- |
| | | Patients | Percent | Patients | Percent |
| All Selected: | | 73/192 | 38 | 66/164 | 40 |
| | Hypertensive | 22/35 | 63 | 38/75 | 47 |
| | Hypertensive & Serum creatinine >1.4 | 6/7 | 86 | 10/12 | 83 |
| | Hypertensive & Serum creatinine >1.4 Albuminuria >20 ug/ml | 6/6 | 100 | 9/10 | 90 |

EXAMPLE 4

Use of the novel RhC immune complex-capturing protein as a first step in capturing and identifying NRIg in a solid-phase EIA assay In the following example, the immune complex-binding protein RhC was substituted for the IgM monoclonal antibody used in step a. of the EIA assay outlined in Example 3 above. Except for this major modification, and several other modifications as described below, the remainder of the EIA was performed similarly to that described above in Example 3 for the detection of NRIg using a dual monoclonal antibody sandwich assay.

RhC protein. The novel immune complex-capturing reagent referred to as "RhC" was derived from horse (equine) serum and is described in detail in U.S. Pat. No. 4,783,528, the entire content of which is incorporated in this application by reference. The stock solution of RhC was prepared at 20 mg/ml in a storage buffer which consisted of 50 mM TRIS (free base), $1 \times 10^{-3}$M ethylenediaminetetraacetate (EDTA), and 0.5M sodium chloride (NaCl) at a final pH of 8.0–8.2. This stock solution was sterilized by filtration through a 0.2-micron ultrafilter and then stored at 4° C. (never frozen). Just prior to use, the stock RhC was diluted to 20 ug/ml in TRIS coating buffer.

TRIS coating buffer. This particular buffering solution is essential for the satisfactory binding of the RhC protein to the flat well bottoms of Immulon-2 microtest plates (Dynatech Laboratories). The buffer was made by dissolving the following salts in deionized water to final concentrations of exactly 50 mM TRIS buffer (in free base form), $1 \times 10^{-3}$M EDTA, and 0.15M NaCl. The pH of this solution was not adjusted after mixing, and was approximately 9.4–9.5.

Coating of the EIA plates with RhC solution. Exactly 100 ul of RhC solution at 20 ug RhC/ml was placed into each well of an Immulon-2 EIA plate and incubated for 18 hours (overnight) at room temperature (approximately 25° C.). Incubation at room temperature is essential, because coating EIA plates with this RhC solution at either 4° C. or 37° C. is not effective.

Buffer for dilution of body fluid samples and for all plate washes (=dilution/wash buffers. The dilution/wash buffer solution was prepared by dissolving in deionized water the following substances to the final concentrations shown: 20 mM TRIS buffer (containing the free base form of TRIS), 0.15M NaCl, and 0.05% Tween-20 detergent. The pH of this solution was adjusted to exactly pH 8.0 with concentrated hydrochloric acid (HCl). This buffer was also used for diluting the enzyme-conjugated monoclonal antibody which was used to mark any NRIg which had been captured on the plates by the solid-phase RhC.

EIA procedure using solid-phase RhC. The process of Example 3 was followed, except that:

a) RhC was substituted for the first antibody immobilized onto the EIA plate wells, for the purpose of capturing NRIg;

b) the buffer solution used for all sample dilutions and for all plate washes was the dilution/wash buffer just described; and c) the final enzyme-substrate color reaction was developed by incubation of the assay plates at 37° C. for exactly 30 minutes only, instead of the 60 minutes used in the regular EIA of Example 3 above.

TABLE 11

The range of concentrations of NRIg in the urines of diabetic patients as detected in EIA assays which used either IgM monoclonal antibody or RhC as the NRIg capturing reagent

| Range of O.D. readings in the EIA assay | Reagent Used to Capture NRIg from Urine | |
|---|---|---|
| | IgM | RhC |
| 0.000–0.200 | 26** | 16** |
| 0.201–0.226 | 6 | 11** |
| 0.227–0.500 | 17 | 37 |
| 0.501–1.000 | 20 | 14 |
| 1.001–2.000 | 7 | 10 |
| 2.001–3.000 | 17 | 5 |
| Total Number of Donors Tested: | 93 | 93 |

**These samples are within the range of normal optical density (O.D.) values obtained in testing urines obtained from a group of 25 normal, healthy donors which yielded the following control values: O.D. readings for IgM capture: $0.108 \pm 0.024$ (range 0.084–0.212); for RhC capture: $0.099 \pm 0.024$ (range 0.068–0.133). Therefore, the upper limit for negative values for the IgM capture assay was an O.D. of 0.200; for the RhC capture assay, it was an O.D. of 0.226.

These data reveal the variation in the levels of detectable NRIg in urines from this group of 93 diabetic patients. With the normal values established for these assays as shown in the footnote to Table 11, it was determined that using the IgM capture assay, 67/93 diabetics had elevated levels of NRIg in their urines, whereas this number was 66/93 when the RhC capture assay was used. This overall agreement was excellent.

When individual urine samples were tested, however, it was important to determine how often the two assay approaches were in agreement from sample to sample. As shown in Table 12, agreement was excellent.

TABLE 12

Capacity of the RhC capture assay and the IgM Monoclonal Antibody Capture Assay to detect NRIg in the same urine samples

| Donor Group | No. of Urine Samples | Agreement between detection results of both assays | Disagreement beween assays as follows: | |
|---|---|---|---|---|
| | | | RhC (−) IgM (+) | RhC (+) IgM (−) |
| Normal donors* | 25 | 24/25 (96%) | 1/25 (4%) | 0 |
| Diabetics, all | 93 | 84/93 (91%) | 5/93 (5%) | 4/93 (4%) |
| normal range: | 26 | 22/26 (85%) | 0 | 4/26 (15%) |
| elevated range: | 67 | 62/67 (93%) | 5/67 (7%) | 0 |

TABLE 12-continued

Capacity of the RhC capture assay and the IgM Monoclonal
Antibody Capture Assay to detect NRIg in the same urine samples

| Donor Group | No. of Urine Samples | Agreement between detection results of both assays | Disagreement beween assays as follows: | |
|---|---|---|---|---|
| | | | RhC (−) IgM (+) | RhC (+) IgM (−) |

*Age range 16–60 yrs; all were clinically healthy individuals. Diabetic urine specimens were selected to represent a wide range of results in the monoclonal antibody capture assay (from <.199 to >3.0. and were not selected based on severity or duration of disease.

EXAMPLE 5

Use of anti-NRIg antibodies in a radial immunodiffusion assay to identify and quantify NRIg in a body fluid The technique of single radial immunodiffusion (RID) is still frequently used as a quantitative measurement of a variety of soluble proteins including, for example, albumin, immunoglobulins and other serum or urine proteins. The following prophetic example demonstrates the capacity of polyclonal anti-NRIg antibodies, made according to the procedures outlined in Example 2 above, to bind to and specifically identify NRIg contained in a microsample of a body fluid, as measured in an RID assay.

Although described here for use with polyclonal antibodies, it is clear to one skilled in the art that the RID assay for NRIg can readily be performed in gels containing one or more monoclonal antibodies to the antigen of interest. In a preferred embodiment, the RID assay plate is designed to have individual test sections, each of which contains antibodies in a separate agarose gel useful for the simultaneous and quantitative detection of distinct protein markers of interest (e.g., NRIg, albumin, and adenosine deaminase binding protein) which may be contained simultaneously in the same body fluid. Such parallel assays allow for the comparison of and correlation between the usefulness of different types of measurements for the very early detection of kidney disease.

A 0.75% (weight/volume) agarose solution is prepared by mixing 750 mg dry agarose powder (EEO (-M$_r$) 0.10, Fisher Scientific Company, Fair Lawn, N.J.) in 100 ml of 16 mM sodium barbital solution containing 2 mM calcium lactate and 0.1% (w/v) sodium azide, pH 8.5 (McDonald et al., *Analytical Biochemistry* 186: 165–168, 1990). This stock agarose solution can also be prepared in phosphate-buffered saline with satisfactory results. This mixture is autoclaved at 120° C. for 30 minutes, both to sterilize the solution and to dissolve the agarose powder. The liquid solution is placed in a water bath and cooled to exactly 52° C., at which time it is thoroughly mixed with an equal volume of prewarmed (52° C.) diluted anti-NRIg antiserum. Additional agarose solutions are similarly prepared which contain antibodies to other urine proteins of interest, such as albumin. The agarose/antibody mixture is carefully poured onto a prewarmed gel frame, avoiding air bubbles, and cooled slowly to room temperature. The gels solidify at room temperature (approximately 25° C.), and are covered and kept in a refrigerator until used.

Just prior to use, a sufficient number of 2.5-mm holes are cleanly punched into each of the agarose gels at a distance of 1.5 cm between centers to allow for tests of the standard control samples, as well as the test body fluid samples. A volume of exactly 5 ul from each body fluid sample to be tested is placed carefully into the appropriate number of separate wells. The volumes of all standards and sample solutions are precisely the same. The plate is then incubated in a moist chamber at room temperature for 24 and 48 hours until the visible ring of precipitation for the most concentrated of the positive control standards has stopped expanding, i.e., reached its plateau in size. At this point, the diameter of each of the various control and test rings observed in the gel is measured twice at right angles, using a low power eyepiece containing a micrometer scale; the two measurements at right angles compensate for any irregularities (noncircularity) in the development of the rings. The two measurements for each ring diameter are then averaged and recorded for each well in the RID assays.

On arithmetic graph paper, the concentrations of the known positive-control standards are plotted on the X (horizontal) axis and the square of the diameter ($D^2$) of the standards is plotted on the Y (vertical) axis; on semilogarithmic paper, the concentration of the standards is plotted on the logarithmic axis and the average diameter (not squared) is plotted on the arithmetic axis. A smooth curve is fitted to the points, forming a standard curve which precisely relates protein concentration (on one axis) to the diameter of a preciptiation ring in the agarose gel of the assay (as shown on the other axis of the graph). The exact concentration of any NRIg in each test sample of urine is then determined by locating the diameter of the ring for that test sample on the standard curve, and reading down to the lower (X) axis of the graph to get the precise protein concentration of that sample.

The concentrations of the various proteins which have been simultaneously measured in the different parts of the RID assay are compared, and correlations are then made between the detectability and concentrations of these proteins, and the degree of nephropathy in the donor of the body fluid tested.

What is claimed is:

1. A monoclonal antibody, or antigen-binding fragment thereof, which specifically binds to native or purified human nephropathy related immunoglobulin glycoprotein and which binds specifically to an antigenic determinant on neuropathy related immunoglobulin glycoprotein, said antigenic determinant being defined by reactivity with a monoclonal antibody selected from the group consisting of the monoclonal antibody produced by American Type Culture Collection (ATCC) hybridoma cell line deposit No. HB-10490 and the monoclonal antibody produced by ATCC hybridoma cell line deposit No. HB-10491.

2. The hybridoma cell line having ATCC deposit number HB-10490.

3. The monoclonal antibody produced by the hybridoma cell line having ATCC deposit number HB-10490.

4. The hybridoma cell line having ATCC deposit number HB-10491.

5. The monoclonal antibody produced by the hybridoma cell line having ATCC deposit number HB-10491.

6. A novel composition of matter comprising a complex which contains a monoclonal antibody of claim 1 bound to human nephropathy related immunoglobulin glycoprotein, wherein said complex is either free in solution or is immobilized onto an inert substrate.

* * * * *